(12) United States Patent
Aubin et al.

(10) Patent No.: US 7,516,651 B2
(45) Date of Patent: Apr. 14, 2009

(54) METHOD AND APPARATUS TO DETERMINE MOISTURE CONTENT IN SOLID INSULATION

(75) Inventors: Jacques Aubin, Montreal (CA); Claude Beauchemin, Valleyfield (CA); Nagui Kamel, Ville St. Laurent (CA)

(73) Assignee: General Electric Company, Schenectady, NY (US)

( * ) Notice: Subject to any disclaimer, the term of this patent is extended or adjusted under 35 U.S.C. 154(b) by 268 days.

(21) Appl. No.: 11/453,516

(22) Filed: Jun. 15, 2006

(65) Prior Publication Data

US 2007/0289367 A1 Dec. 20, 2007

(51) Int. Cl.
*G01N 5/02* (2006.01)
(52) U.S. Cl. .................... 73/73; 73/74; 73/75
(58) Field of Classification Search .......... 73/73, 73/74, 75
See application file for complete search history.

(56) References Cited

U.S. PATENT DOCUMENTS 5,343,045 A * 8/1994 Gupta ............... 250/339.1
6,401,518 B1 * 6/2002 O'Keeffe et al. ........... 73/19.01
6,779,385 B2 * 8/2004 Belanger ..................... 73/73
6,906,630 B2 6/2005 Georges et al. ............ 340/646
2004/0007052 A1 * 1/2004 Belanger ..................... 73/73
2004/0159146 A1 * 8/2004 Belanger ..................... 73/73

FOREIGN PATENT DOCUMENTS

| EP | 0 628 803 A3 | 4/1994 |
|---|---|---|
| WO | WO 2004/008129 A2 | 1/2004 |
| WO | WO 2004/008129 A3 | 1/2004 |

* cited by examiner

*Primary Examiner*—Hezron Williams
*Assistant Examiner*—Gunnar J Gissel
(74) *Attorney, Agent, or Firm*—Cantor Colburn LLP

(57) ABSTRACT

Disclosed herein is a method that relates to determining water content of a solid insulation at a specific location within a transformer. The method comprising, determining a temperature of the solid insulation at a specific location, calculating a relative moisture saturation of the oil at the specific location, calculating the ultimate water content in the solid insulation at the specific location, and calculating an actual water content in the solid insulation at the specific location.

15 Claims, 4 Drawing Sheets

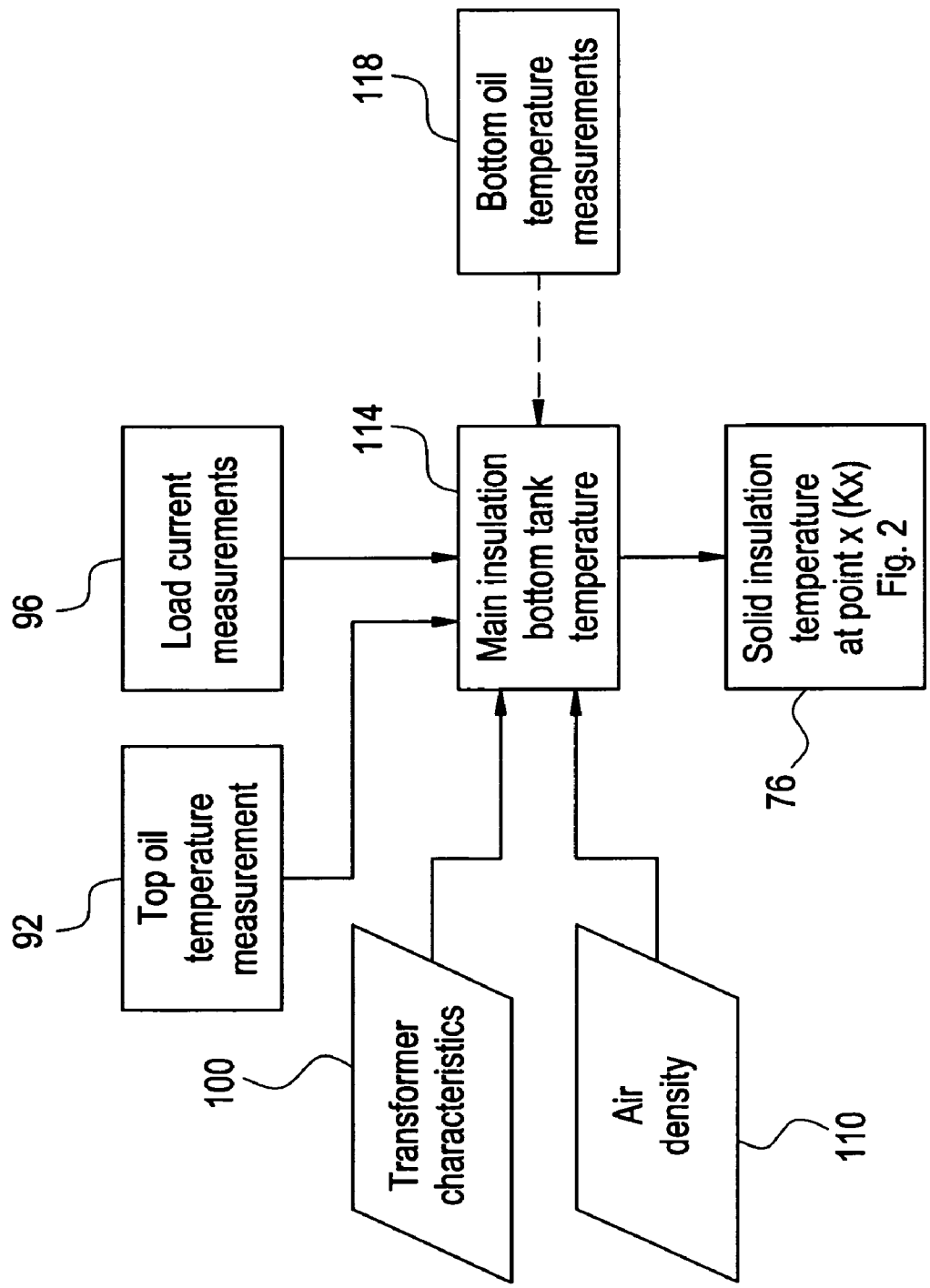

METHOD AND APPARATUS TO DETERMINE MOISTURE CONTENT IN SOLID INSULATION

BACKGROUND OF THE INVENTION

Moisture management in power transformers is a persistent concern especially for aging units. Extensive drying procedures are applied at the manufacturing stage and sustained efforts are deployed in service to maintain high dryness. Excessive moisture in solid or liquid insulations can lead to significant reductions of dielectric strength and reduce the partial discharge inception level. The effect of moisture on insulation aging has been well documented. It has also been demonstrated that at high temperatures, the residual moisture in winding insulation can trigger the release of free gas bubbles, thus creating an immediate threat to the dielectric integrity of the insulation structure. Assessment of water content in solid insulation is rightfully an essential part of any comprehensive condition assessment program.

A traditional method of moisture monitoring calls for oil sampling at regular intervals. The oil sample is then processed through a Karl Fischer titration method that provides the total water content in oil in parts per million (ppm). Most of the water is in the form of dissolved water and is available to move from the oil to the solid insulation as the transformer progresses toward equilibrium. However some of the measured water is chemically bound to chemical agents such as by-products of oxidation. This bound water is only partially available to migrate from the oil to the paper. As the oil ages, the quantity of chemical agents due to oxidation increases and these agents provide additional sites for the water to bind. Some of the water may also bind to particles in suspension in the oil, and this water would not be fully available to move to the solid insulation. Equilibrium curves have been developed and are used to relate absolute water content in oil to water content in paper. Application of these curves implies that the transformer is under thermal equilibrium. In fact this is rarely the case since the temperatures within a transformer are almost continuously changing based on changes in the ambient temperature and the electrical loads applied. In spite of these constraints, this method remains the most commonly used to assess the moisture content of solid insulation.

In recent years, on-line sensors for measuring the moisture content in oil have been developed. Such sensors are typically submerged in the oil and measure capacitance that is then correlated to moisture content for the oil. The moisture content in oil is then converted into moisture content in paper using equilibrium curves. This method is very approximate since it assumes that the transformer is under thermal equilibrium. However, with temperature of the transformer changing almost continuously with the variations of ambient temperatures and operational load changes, equilibrium is rarely ever achieved. Further, significant temperature gradients exist within a transformer resulting in associated variations in moisture content.

Accordingly, there is a need in the art for a system and method of determining accurate water content of solid insulation in transformers even as the temperature of the solid insulation is continuously varying. Additionally there is need to determine the water content of solid insulation at different locations within a transformer even though the water content of the solid insulation at each location may differ.

BRIEF DESCRIPTION OF THE INVENTION

Disclosed herein is a method that relates to determining water content of a solid insulation at a specific location within a transformer. The method comprising, determining a temperature of the solid insulation at a specific location, calculating a relative moisture saturation of the oil at the specific location, calculating the ultimate water content in the solid insulation at the specific location, and calculating an actual water content in the solid insulation at the specific location.

Further disclosed herein is a system that relates to monitoring actual water content of a solid insulation at a specific location within a transformer. The system comprising, a first temperature sensor to measure the temperature of oil within the transformer at a first location and a device to measure a moisture content of the oil at the first location. A second temperature sensor to measure the temperature of oil at the specific location, and a processor for receiving inputs from sensors and calculating the actual water content of the solid insulation at the specific location.

Further disclosed herein is a computer program product that relates to calculating an actual water content of a solid insulation at a specific location within a transformer in a computer environment. The computer program product comprising a storage medium readable by a processing circuit and storing instructions for execution by the processing circuit for facilitating a method. The method comprising, receiving data of moisture content of oil that circulates within the transformer, receiving data of temperature of the oil where the moisture content is measured, and receiving data of temperature of the solid insulation at the specific location. Using the data received in calculating a relative moisture saturation of the oil at the specific location, calculating an ultimate water content in the solid insulation at the specific location, and calculating an actual water content in the solid insulation at the specific location.

BRIEF DESCRIPTION OF THE DRAWINGS

FIG. 4 depicts a flow chart disclosing an alternate means for determining the temperature of a solid insulation for input to the chart of FIG. 2.

DETAILED DESCRIPTION OF THE INVENTION

Figure 1:
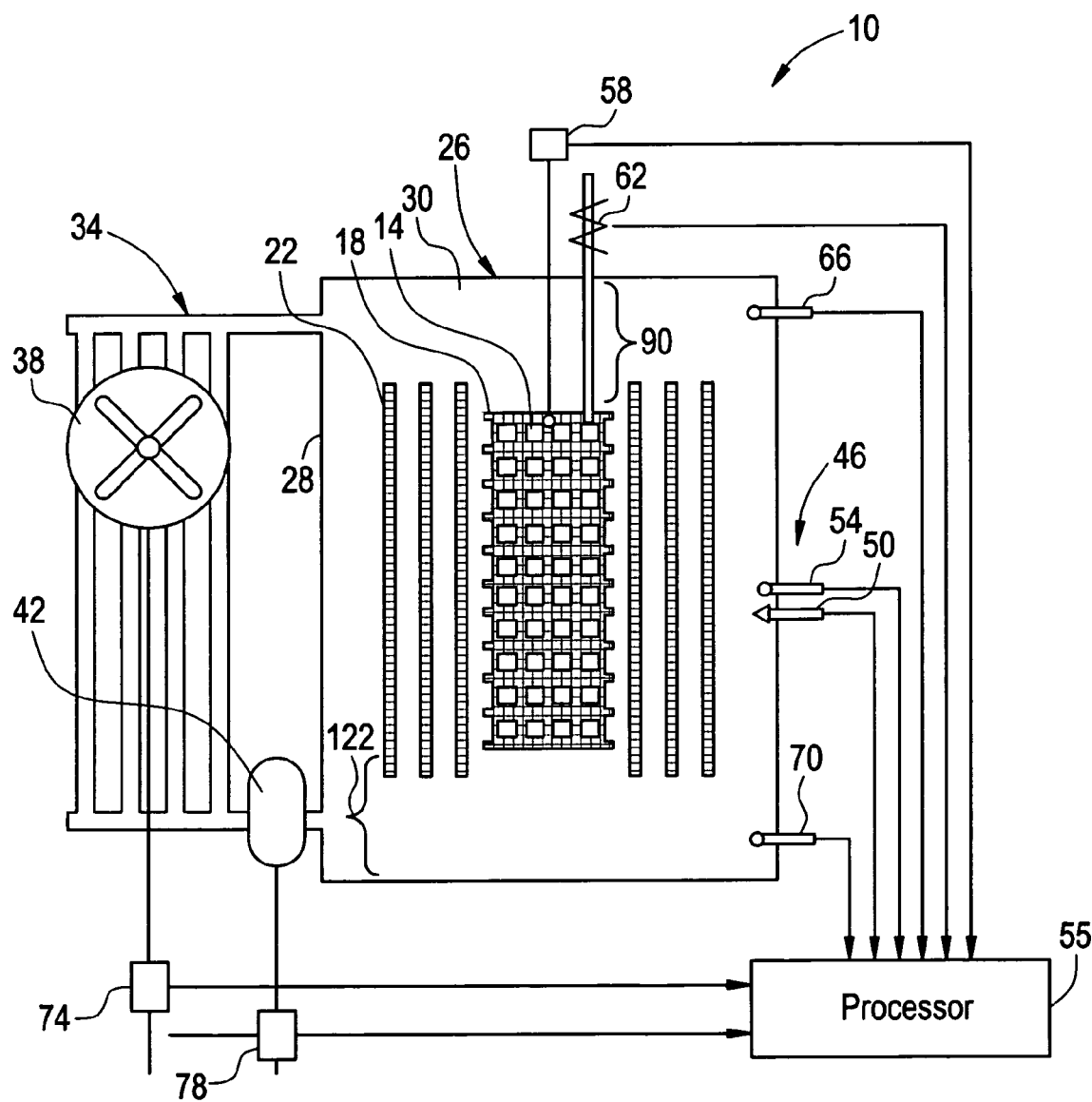
FIG. 1 depicts a schematic of a transformer disclosed herein.

Referring to FIG. 1, a schematic of a power transformer according to an embodiment of the present invention is depicted generally at 10. It should be understood, however, that embodiments of the invention may also be applied to other similar types of oil immersed electrical equipment such as distribution transformers, regulating transformers, shunt reactors, converter transformers, instrument transformers, generating station units and instrument transformers. One of several windings 14, made of a conductive material, is wrapped in solid insulation material 18 sometimes referred to herein as paper even though paper is only one possible material that may be used as solid insulation. Main solid insulation 22 is positioned between the windings 14 and a tank 26 with tank walls 28. The windings 14 and solid insulations 18, 22 are immersed in insulating oil 30. The transformer 10 may include a cooling system 34 with fans 38 and pumps 42 that are activated as required by a cooling control system (not shown). The transformer 10 also includes various sensors for use in calculating the moisture content of the solid insulation 18, 22. For example, a moisture-in-oil probe 46 comprises; a water-in-oil sensor 50 and a temperature sensor 54 to measure the oil temperature at the water-in-oil sensor 50 location. The transformer 10 also includes a processor 55 in electrical communication with at least the foregoing sensors for receiving data from the sensors and processing the data.

Figure 3:
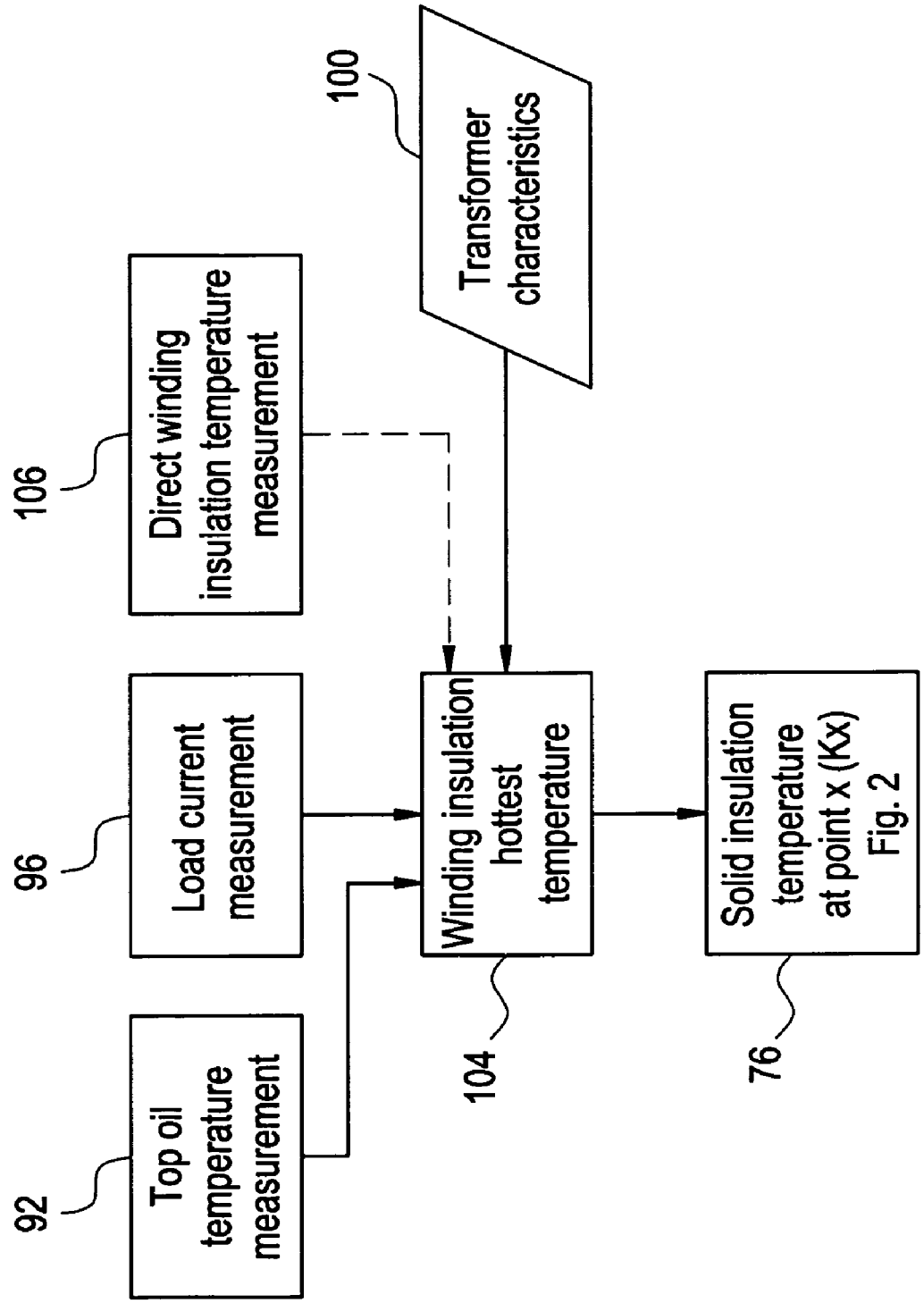
FIG. 3 depicts a flow chart for determining the temperature of a solid insulation for input to the chart of FIG. 2.

In order to calculate the moisture content in the solid insulation 18, 22, among other things, the temperature of the solid insulation 18, 22 must be known. Determination of the solid insulation temperature may be measured directly or can be calculated based on inputs from other sensors. To measure the temperature of the solid insulation 18, 22 directly, non-conductive devices such as fiber optic temperature probes 58, for example, may be utilized. To calculate the temperature of the solid insulation 18, 22, inputs from the following sensors are utilized: current meter 62, to measure the load current on one or several windings 14; temperature sensor 66, to measure the temperature of the oil 30 in a top portion of the tank 90; temperature sensor 70, to measure the temperature of the oil 30 in a bottom portion of the tank 122; fan operating sensor 74 and/or pump operating sensor 78. Additionally, the air density 110, based on the location where the transformer 10 is installed, is inputted as a fixed parameter to the system. Methods for calculating the temperature of the solid insulation 18, 22, at specific locations will be discussed further in reference to FIGS. 3 and 4.

Before the actual moisture content of the solid insulation 18, 22 at a specific location can be calculated; the ultimate water content of the solid insulation 18, 22 must first be determined. However, before the ultimate water content of the solid insulation 18, 22 can be determined the relative oil saturation must be known where the oil 30 makes contact with the solid insulation 18, 22. Once the actual moisture content has been established, the effect of such moisture content on; insulation aging, threshold temperature for the release of free bubbles of water vapor, and reduction of dielectric strength, may be calculated using known methods.

Figure 2:
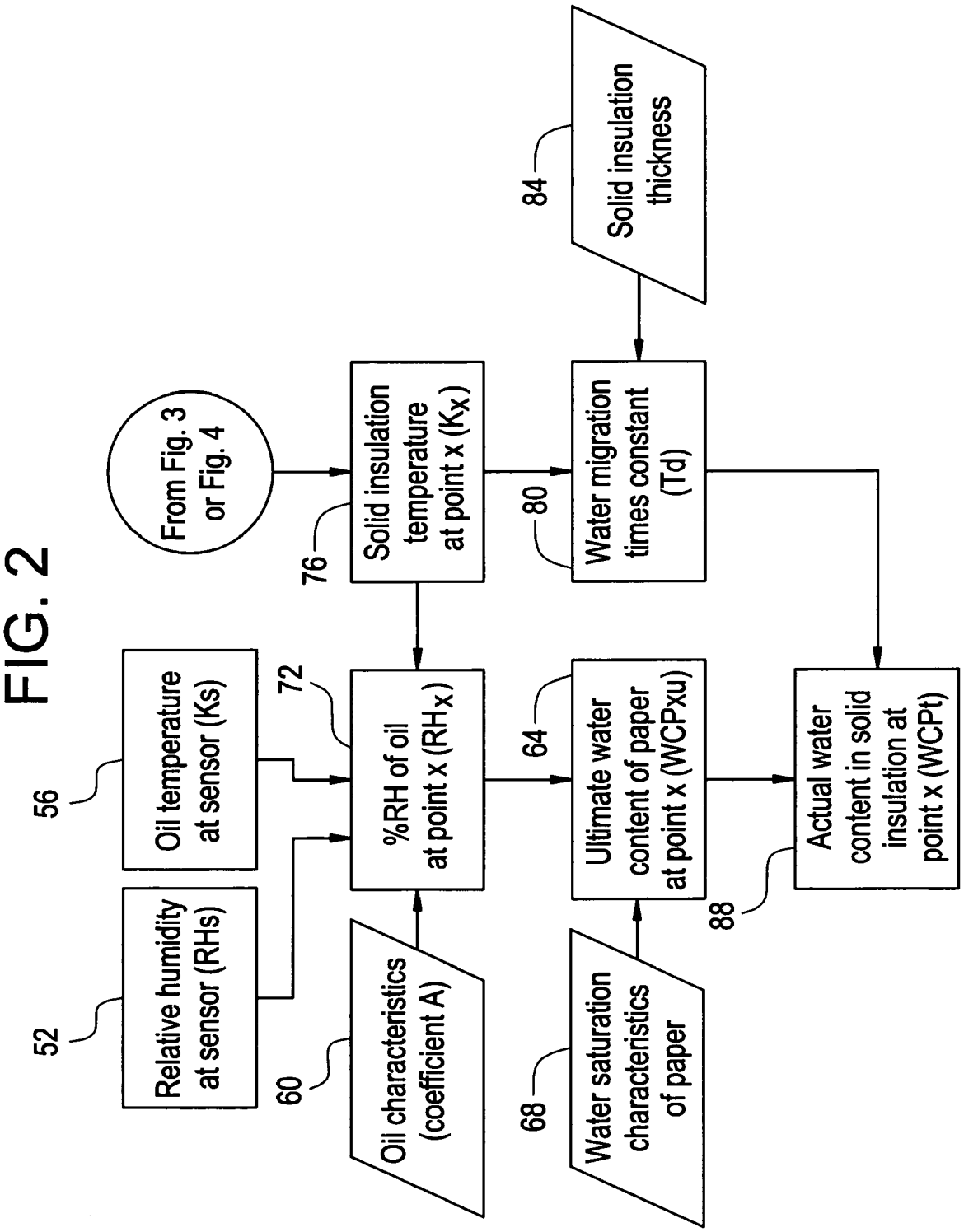
FIG. 2 depicts a flow chart for calculating the moisture content in a solid insulation disclosed herein.

Referring to FIG. 2 a flow chart showing how to calculate the moisture content in the solid insulation 18, 22 is depicted. The water-in-oil sensor 50 provides a relative humidity value 52 for the oil 30. Specifically, the water-in-oil sensor 50 determines the amount of water present in the oil 30, in regard to the total amount of water that the oil 30 could carry when saturated at whatever temperature the oil 30 is at in that particular location. This relative humidity value 52 is expressed as RHs (for Relative Humidity at the water-in-oil sensor 50) and generally is expressed in percent RH. The oil temperature sensor 54 measures the oil temperature 56 at the location of the water-in-oil sensor 50. This temperature is converted into absolute temperature Ks (in degrees Kelvin) and is used to calculate the relative humidity at specific locations of interest.

The relative humidity at any point x in the transformer 10 can be calculated, as long as the absolute temperature Kx at the point x is known, by the following equation:

$$RHx = RHs * EXP(A(1/Ks - 1/Kx))$$

where A is a coefficient dependant upon specific oil characteristics 60.

The ultimate water content in paper at location x (sometimes referred to as WCPxu) 64, is calculated from known functions of saturation of water in paper as a function of temperature 68, and the value of the relative humidity of oil at point x (sometimes referred to as RHx) 72, per the following equation:

$$WCPxu = POWER(10, (Ax + Bx/Kx))$$

where Ax and Bx are polynomial functions of the 5th order derived from RHx 72 and the solubility functions of water in paper as a function of temperature 68, and Kx 76 is the absolute temperature (in Kelvin) at point x.

The word "ultimate" is used to describe the ultimate water content in paper, because this level of water content in the paper would be reached only if the temperature of the oil 30 and the paper 18, 22 remained stable for an infinite period of time. The time required to approach stability is known for several types of transformer components using thin solid insulation material 18. This time requirement may vary from several hours to several years depending on parameters such as, for example, the particular solid insulation material employed, the material's thickness, and the material's temperature. In an embodiment of the present invention it was found that a water migration time constant (Td) 80 for the solid insulation 18, 22 could be reduced to an exponential function and calculated by the equation:

$$Td = L^2 * C * EXP(D * Tx)$$

where L is the equivalent thickness of the solid insulation in mm 84, C and D are coefficients determined experimentally and Tx is the temperature (in Celsius) of the solid insulation material.

The actual water content in the solid insulation at time t (sometimes referred to as WCPt) 88 is then calculated from the WCPxu 64 and the migration time constant (Td) 80. This can be done using an incremental calculation where the actual water content in solid insulation at time t (sometimes referred to as WCPt) 88 is determined incrementally based on the previously calculated value of WCPt 88 at time t−1, using a time increment between successive calculations of dt and the migration time constant (Td) 80:

$$WCPt = WCPt-1 + (WCPxu - WCPt-1) * (1 - EXP(-dt/Td))$$

Alternatively, the actual value of the water content in solid insulation at time t (WCPt) 88 can be calculated using the following low pass filter equation:

$$WCPt = WCPt-1 + (WCPxu - WCPt-1) * (dt/E * Td)$$

where E is an experimental coefficient.

The foregoing equations will be applied to two specific locations of significant interest within a transformer 10. A first location of particular interest is a top portion of the tank 90, which is typically the hottest part of the winding solid insulation 18. An embodiment describing the temperature calculation method for this location is presented schematically in FIG. 3. The top of the transformer tank oil temperature 92 can be measured with the top oil temperature sensor 66 (see FIG. 1). The load current 96 in the winding under observation can be measured with the current meter 62 (see FIG. 1). These two values can be combined in a known fashion using appropriate transformer characteristics 100 to derive what is usually the hottest winding solid insulation temperature 104.

Alternatively, the fiber optic temperature probe 58 (see FIG. 1), or similar temperature measuring device, can be inserted to the winding solid insulation 18, in the known hottest area, to provide a direct temperature measurement 106 of what is usually the hottest winding solid insulation 18.

The winding solid insulation temperature 104 is then used as the solid insulation temperature at point x 76 for the calculations of FIG. 2.

A second location of particular interest in the transformer 10 is the main solid insulation 22 providing dielectric strength between the windings 14 and the transformer tank 26. The area of most interest is the main solid insulation 22 in the bottom portion of the tank 122 since the temperature is cooler than elsewhere in the transformer 10 and the moisture content is therefore higher. An embodiment of a calculation of temperature for the main solid insulation 22 in this bottom portion of the tank 122 is presented schematically in FIG. 4.

As described above, the top portion of the tank 90 oil temperature 92 can be measured with the top oil temperature sensor 66, and the load current 96 in the winding under observation can be measured with the current meter 62. The cooling fan operating sensor 74 and the cooling pump operating sensor 78 of the cooling system 34 are used to select the proper transformer characteristics 100. The air density 110 in the location where the transformer 10 is installed is used to adjust thermal characteristics accordingly. The foregoing parameters are used in a known fashion to calculate the main solid insulation bottom tank temperature 114.

Alternatively, the temperature sensor 70 can be used to directly measure the temperature 118 of the oil 30 in the bottom portion of the tank 122, which is known to be similar in temperature to that of the main solid insulation 22 in the bottom portion of the tank 122.

The main insulation bottom tank temperature 114 is then used as the solid insulation temperature at point x 76 in FIG. 2.

The embodiments disclosed have illustrated how the moisture content of the solid insulation may be calculated at two specific locations within the transformer 10. It should be noted, however, that the methods disclosed herein can be used to compute the moisture content of solid insulation at any location within the transformer 10 for which a temperature can be calculated or measured.

Embodiments of the invention may be in the form of computer-implemented processes and apparatuses for practicing those processes. In exemplary embodiments, the invention is embodied in computer program code. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. The technical effect of the executable instructions is to calculate an actual water content of a solid insulation in a transformer at a specific location within the transformer.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What is claimed is:

1. A method of determining water content of a solid insulation at a specific location within a transformer, the method comprising:
   determining a temperature of the solid insulation at a specific location;
   calculating a relative moisture saturation of the oil at the specific location;
   calculating the ultimate water content in the solid insulation at the specific location; and
   calculating an actual water content in the solid insulation at the specific location.

2. The method of claim 1, further comprising:
   calculating the actual water content of the solid insulation during thermal transients of the transformer.

3. The method of claim 1, further comprising:
   measuring the temperature of the solid insulation at the specific location.

4. The method of claim 1, further comprising:
   calculating the temperature of the solid insulation at the specific location using appropriate transformer characteristics and a measured oil temperature at the specific location and a measured current load in a winding under consideration.

5. The method of claim 1, further comprising:
   calculating the temperature of the solid insulation at the specific location using appropriate transformer characteristics, determined in part from at least one cooling system sensor, a measured oil temperature at the specific location, a measured current load in a winding under consideration, and a density of the air.

6. The method of claim 1, further comprising:
   measuring the relative humidity of the oil with a water-in-oil sensor at a location of a temperature sensor;
   measuring a temperature of the oil at the location of the water-in-oil sensor;
   calculating an absolute temperature at the location of the water-in-oil sensor from the measured temperature of the oil at the location of the water-in-oil sensor;
   measuring a temperature of the oil at the specific location;
   calculating the absolute temperature of the oil at the specific location from the measured temperature of the oil at the specific location; and
   calculating the relative humidity of the oil at the specific location using the relative humidity at the water-in-oil sensor, the absolute temperature at the water-in-oil sensor and the absolute temperature at the specific location.

7. The method of claim 1, further comprising:
   calculating the ultimate water content in the solid insulation at the specific location using water saturation characteristics of the solid insulation material, a relative humidity of oil at the specific location and an absolute temperature at the specific location.

8. The method of claim 1, further comprising:
   calculating the actual water content in the solid insulation at the specific location using a migration time constant characterizing the exchange of water between the oil and the solid insulation and an ultimate water content in the solid insulation at the specific location.

9. The method of claim 1, further comprising:

measuring moisture content of an oil that circulates within the transformer;

measuring a temperature of the oil where the moisture content of the oil is measured.

10. A system for monitoring actual water content of a solid insulation at a specific location within a transformer, the system comprising:
- a first temperature sensor to measure the temperature of oil within the transformer at a first location;
- a device to measure a moisture content of the oil at the first location;
- a second temperature sensor to measure the temperature of oil at the specific location;
- a processor for receiving inputs from sensors and calculating the actual water content of the solid insulation at the specific location.
- a current sensor in signal communication with the processor; and
- at least one cooling system sensor in signal communication with the processor.

11. The system of claim 10, wherein:
the specific location is at a solid insulation of a winding of the transformer.

12. The system of claim 11, wherein:
the solid insulation is at a top portion of a tank of the transformer.

13. The system of claim 10, wherein:
the specific location is at a main solid insulation between a winding and a tank wall of the transformer.

14. The system of claim 13, wherein:
the main solid insulation is at a bottom portion of a tank of the transformer.

15. A computer program product for calculating an actual water content of a solid insulation at a specific location within a transformer in a computer environment, the computer program product comprising a storage medium readable by a processing circuit and storing instructions for execution by the processing circuit for facilitating a method comprising:
- receiving data of moisture content of oil that circulates within the transformer;
- receiving data of temperature of the oil where the moisture content is measured;
- receiving data of temperature of the solid insulation at the specific location;
- calculating a relative moisture saturation of the oil at the specific location;
- calculating an ultimate water content in the solid insulation at the specific location; and
- calculating an actual water content in the solid insulation at the specific location.

* * * * *